(12) United States Patent
Cezanne et al.

(10) Patent No.: US 7,951,804 B2
(45) Date of Patent: May 31, 2011

(54) PIPERIDINYL COMPOUNDS

(75) Inventors: Bertram Cezanne, Mörfelden-Walldorf (DE); Dieter Dorsch, Ober-Ramstadt (DE); Werner Mederski, Zwingenberg (DE); Christos Tsaklakidis, Weinheim (DE); Johannes Gleitz, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 955 days.

(21) Appl. No.: 10/582,850

(22) PCT Filed: Nov. 19, 2004

(86) PCT No.: PCT/EP2004/013202
§ 371 (c)(1),
(2), (4) Date: Jun. 14, 2006

(87) PCT Pub. No.: WO2005/056528
PCT Pub. Date: Jun. 23, 2005

(65) Prior Publication Data
US 2007/0123509 A1    May 31, 2007

(30) Foreign Application Priority Data
Dec. 15, 2003 (DE) .................... 103 58 539

(51) Int. Cl.
*A61K 31/535* (2006.01)
*A61K 31/497* (2006.01)
*A61K 31/545* (2006.01)
*C07D 413/00* (2006.01)
*C07D 401/00* (2006.01)
*C07D 211/08* (2006.01)

(52) U.S. Cl. ............. 514/235.5; 514/237.2; 514/253.01; 514/317; 544/129; 544/360; 546/192

(58) Field of Classification Search .................. None
See application file for complete search history.

(56) References Cited

U.S. PATENT DOCUMENTS

| | | | |
|---|---|---|---|
| 4,719,200 A | 1/1988 | Eguchi et al. | |
| 5,346,907 A * | 9/1994 | Kerwin et al. | 514/312 |
| 5,721,251 A * | 2/1998 | Chen et al. | 514/318 |
| 5,847,148 A | 12/1998 | Jacobsen et al. | |
| 6,225,309 B1 | 5/2001 | Faull et al. | |
| 7,183,277 B2 * | 2/2007 | Dorsch et al. | 514/231.2 |
| 7,314,883 B2 * | 1/2008 | Chen et al. | 514/320 |
| 7,598,241 B2 * | 10/2009 | Dorsch et al. | 514/228.8 |
| 2003/0144350 A1 | 7/2003 | Stevenson et al. | |
| 2004/0038858 A1 | 2/2004 | Dorsch et al. | |
| 2004/0209821 A1 | 10/2004 | Hamann et al. | |
| 2004/0254374 A1 | 12/2004 | Jones et al. | |

FOREIGN PATENT DOCUMENTS

| | | |
|---|---|---|
| EP | 0 173 510 A | 3/1986 |
| JP | 09 227523 A | 9/1997 |
| WO | WO 96/10022 A | 4/1996 |
| WO | WO 02/48099 A | 6/2002 |
| WO | WO 03/007888 A | 1/2003 |
| WO | WO 03/050109 A | 6/2003 |
| WO | WO 03048154 * | 6/2003 |

OTHER PUBLICATIONS

Vippagunta et al. Advanced Drug Delivery Reviews, 2001, 48, 3-26.*
Turpie. Expert Opinion in Pharmacotherapy, 2004, 5(6), 1373-84.*
Expert Opinion in Investigational Drugs, 2001, 10(12), 2175-83.*
"Cancer definition", http://www.medterms.com/script/main/art.asp?articlekey=2580, accessed Nov. 27, 2007.*
Turpie. Expert Opinion on Pharmacotherapy, 2004, 5(6), 1373-84.*
Hembrough et al. Cancer Research, 2003, 63, 2997-3000.*
Holladay et al. Bioorganic and Medicinal Chemistry Letters, 1995, 5(24), 3057-62.*
Holladay, et al. : "Amino Acid-Derived Piperidides as Novel CCKB Ligands With Anxiolytic-Like Properties"; Bioorganic & Medicinal Chemistry Letters, Oxford, GB, vol. 5, No. 24, 1995, pp. 3057-3062, XP000612646; ISSN: 0960-894X.
Database Chemcats 'Online! Chemical Abstracts Service Columbus, Ohio, US Retrieved From STN; XP002319705 & "Comgenex Product List" Jun. 26, 2003, Comgenex International Inc, Monmouth Jct, NJ.

* cited by examiner

*Primary Examiner* — Noble Jarrell
(74) *Attorney, Agent, or Firm* — Millen, White, Zelano & Branigan, P.C.

(57) ABSTRACT

Novel compounds of the formula (I) in which D, E, Q, T, X, Y, Z, Z', $R^1$, $R^4$ and $R^{4'}$ have the meanings indicated, are inhibitors of coagulation factor Xa and can be employed for the prophylaxis and/or therapy of thromboembolic diseases and for the treatment of tumors.

39 Claims, No Drawings

PIPERIDINYL COMPOUNDS

The invention relates to compounds of the formula I

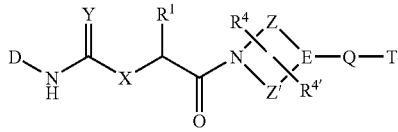

in which
- D denotes a mono- or bicyclic aromatic carbo- or heterocycle having 0 to 4 N, O and/or S atoms which is unsubstituted or mono- or polysubstituted by Hal, A, $OR^2$, $N(R^2)_2$, $NO_2$, CN, $COOR^2$, $CON(R^2)_2$ or —C≡CH,
- X denotes $NR^3$ or O,
- Y denotes O, S, NH, N—CN or N—$NO_2$,
- $R^1$ denotes H, Ar, Het, cycloalkyl or
  A, which may be mono-, di- or trisubstituted by $OR^2$, $SR^2$, $S(O)_m R^2$, $SO_2 N(R^2)_2$, $SO_3 R^2$, $S(=O)(=NR^2)R^2$, $NR^2 SO_2 R^2$, $OSO_2 R^2$, $OSO_2 N(R^2)_2$, $N(R^2)_2$, CN, $COOR^2$, $CON(R^2)_2$, Ar, Het or cycloalkyl,
- E denotes CH or N,
- Z is absent or denotes a $(CH_2)_q$ group, in which one or two $CH_2$ groups may be replaced by N, O and/or S atoms and/or by a —CH=CH— group and which is unsubstituted or monosubstituted by carbonyl oxygen (=O),
- Z' is absent or denotes a $(CH_2)_{q'}$ group, in which one or two $CH_2$ groups may be replaced by N, O and/or S atoms and/or by a —CH=CH— group and which is unsubstituted or monosubstituted by carbonyl oxygen (=O),
- Q is absent or denotes O, $NR^2$, C=O, $SO_2$ or $C(R^2)_n$,
- $R^2$ denotes H, A, $—[C(R^3)_2]_n$—Ar', $—[C(R^3)_2]_n$—Het', $—[C(R^3)_2]_n$-cycloalkyl, $—[C(R^3)_2]_n$—$N(R^3)_2$ or $—[C(R^3)_2]_n$—$OR^3$,
- $R^3$ denotes H or A,
- $R^4$, $R^{4'}$ each, independently of one another, is absent or denote A, OH or OA,
- $R^4$ and $R^{4'}$ together also denote methylene or ethylene,
- T denotes a mono- or bicyclic saturated, unsaturated or aromatic carbo- or heterocycle having 0 to 4 N, O and/or S atoms, which may be mono-, di- or trisubstituted by =O, =S, =NH, =$NR^3$, =$NOR^3$, =$NCOR^3$, =$NCOOR^3$, =$NOCOR^3$, $R^3$, Hal, A, $—[C(R^3)_2]_n$—Ar, $—[C(R^3)_2]_n$-Het, $—[C(R^3)_2]_n$-cycloalkyl, $OR^3$, $N(R^3)_2$, $NO_2$, CN, $COOR^3$, $CON(R^3)_2$, $NR^3 COA$, $NR^3 CON(R^3)_2$, $NR^3 SO_2 A$, $COR^3$, $SO_2 NR^2$ and/or $S(O)_n A$,
- A denotes unbranched or branched alkyl having 1-10 C atoms, in which one or two $CH_2$ groups may be replaced by O or S atoms and/or by —CH=CH— groups and/or also 1-7 H atoms may be replaced by F,
- Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2 COA$, $NR^2 SO_2 A$, $COR^2$, $SO_2 N(R^2)_2$, $—[C(R^3)_2]_n$—$COOR^2$, —O—$[C(R^3)_2]_o$—$COOR^2$, $SO_3 H$ or $S(O)_n A$,
- Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3 COA$, $NR^3 CON(R^3)_2$, $NR^3 SO_2 A$, $COR^3$, $SO_2 N(R^3)_2$, $S(O)_n A$, $—[C(R^3)_2]_n$—$COOR^3$ or —O—$[C(R^3)_2]_o$—$COOR^3$,
- Het denotes a mono- or bicyclic saturated, unsaturated or aromatic heterocycle having 1 to 4 N, O and/or S atoms, which may be unsubstituted or mono-, di- or trisubstituted by carbonyl oxygen (=O), =S, =$N(R^2)_2$, Hal, A, $—[C(R^3)_2]_n$—Ar, $—[C(R^3)_2]_n$-Het', $—[C(R^3)_2]_n$-cycloalkyl, $—[C(R^3)_2]_n$—$OR^2$, $—[C(R^3)_2]_n$—$N(R^3)_2$, $NO_2$, CN, $—[C(R^3)_2]_n$—$COOR^2$, $—[C(R^3)_2]_n$—$CON(R^2)_2$, $—[C(R^3)_2]_n$—$NR^2 COA$, $NR^2 CON(R^2)_2$, $—[C(R^3)_2]_n$—$NR^2 SO_2 A$, $COR^2$, $SO_2 N(R^2)_2$ and/or $S(O)_n A$,
- Het' denotes a mono- or bicyclic saturated, unsaturated or aromatic heterocycle having 1 to 4 N, O and/or S atoms, which may be unsubstituted or mono- or disubstituted by carbonyl oxygen, =S, =$N(R^3)_2$, Hal, A, $OR^3$, $N(R^3)_2$, $NO_2$, CN, $COOR^3$, $CON(R^3)_2$, $NR^3 COA$, $NR^3 CON(R^3)_2$, $NR^3 SO_2 A$, $COR^3$, $SO_2 N(R^3)_2$ and/or $S(O)_n A$,
- Hal denotes F, Cl, Br or I,
- m denotes 1 or 2,
- n denotes 0, 1 or 2,
- o denotes 1, 2 or 3,
- p denotes 1, 2, 3, 4 or 5,
- q, q' each, independently of one another, denote 0, 1, 2, 3 or 4, where
at least one of the groups Z or Z' is present, and
0<q+q'≦6,
and pharmaceutically usable derivatives, solvates, salts, and stereo-isomers thereof, including mixtures thereof in all ratios.

The invention also relates to the optically active forms, the racemates, the diastereomers and the hydrates and solvates, for example alcoholates, of these compounds.

The invention had the object of finding novel compounds having valuable properties, in particular those which can be used for the preparation of medicaments.

It has been found that the compounds of the formula I and salts thereof have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexy, angina pectoris, restenosis after angioplasty and claudicatio intermittens.

The compounds of the formula I according to the invention are furthermore inhibitors of the coagulation factors factor VIIa, factor IXa and thrombin in the blood coagulation cascade.

Other carboxamides are described in WO 02/48099; aromatic amides are described in WO 99/00121 and in WO 00/39118. Aromatic amidine derivatives having an antithrombotic action are disclosed, for example, in EP 0 540 051 B1. Cyclic guanidines for the treatment of thromboembolic diseases are described, for example, in WO 97/08165. Aromatic heterocyclic compounds having factor Xa-inhibitory activity are disclosed, for example, in WO 96/10022. Substituted N-[(aminoiminomethyl)phenyl-alkyl]azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after cross-linking, make an elementary contribution to thrombus formation. Activation of thrombin may result in the occurrence of thromboembolic diseases. However, inhibition of thrombin may inhibit the fibrin formation involved in thrombus formation.

The inhibition of thrombin can be measured, for example, by the method of G. F. Cousins et al. in *Circulation* 1996, 94, 1705-1712.

Inhibition of factor Xa can thus prevent the formation of thrombin.

The compounds of the formula I according to the invention and salts thereof engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220-223.

The inhibition of factor Xa can be measured, for example, by the method of T. Hara et al. in *Thromb. Haemostas.* 1994, 71, 314-319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73-81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089-12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57-59.

The publications listed below describe an antitumour action of TF-VII and factor Xa inhibitors for various types of tumour:
K. M. Donnelly et al. in Thromb. Haemost. 1998; 79: 1041-1047;
E. G. Fischer et al. in J. Clin. Invest. 104: 1213-1221 (1999);
B. M. Mueller et al. in J. Clin. Invest. 101: 1372-1378 (1998);
M. E. Bromberg et al. in Thromb. Haemost. 1999; 82: 88-92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexy, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease. The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used for diseases in which blood coagulation makes a crucial contribution to the course of the disease or represents a source of secondary pathology, such as, for example, in cancer, including metastasis, inflammatory diseases, including arthritis, and diabetes.

The compounds according to the invention are furthermore used for the treatment of migraine (F. Morales-Asin et al., Headache, 40, 2000, 45-47).

In the treatment of the diseases described, the compounds according to the invention are also employed in combination with other thrombolytically active compounds, such as, for example, with "tissue plasminogen activator" t-PA, modified t-PA, streptokinase or urokinase. The compounds according to the invention are administered either at the same time as or before or after the other substances mentioned.

Particular preference is given to simultaneous administration with aspirin in order to prevent recurrence of the thrombus formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to Claim 1 and salts thereof, characterised in that
a) for the preparation of compounds of the formula I
  in which
  X denotes NH and
  Y denotes O,
a compound of the formula II

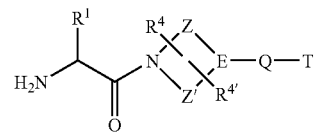

in which
$R^1$, $R^4$, $R^{4'}$, E, Q, T, Z and Z' have the meanings indicated in Claim 1,
is reacted with a compound of the formula III

in which
D has the meaning indicated in Claim 1,
or
b) for the preparation of compounds of the formula I
  in which
  X and Y denote O, a compound of the formula IV

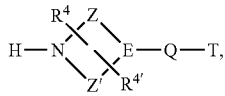

in which W, Y and T have the meaning indicated in Claim 1, is reacted with a compound of the formula V

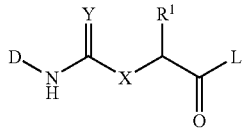

in which
X and Y denote O,
L denotes Cl, Br, I or a free or reactively functionally modified OH group and
$R^1$ and D have the meanings indicated in Claim 1,
and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alcoholates.

The term pharmaceutically usable derivatives is taken to mean, for example, the salts of the compounds according to the invention and also so-called prodrug compounds.

The term prodrug derivatives is taken to mean compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, their meanings are independent of one another.

Above and below, the radicals or parameters D, E, Q, T, X, Y, Z, Z', $R^1$, $R^4$, $R^{4'}$ have the meanings indicated under the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1-6 C atoms, preferably methyl, ethyl, propyl, isopropyl, butyl, isobutyl, sec-butyl, tert-butyl, pentyl, hexyl or trifluoromethyl.

Cycloalkyl has 3-7 C atoms and preferably denotes cyclopropyl, cyclobutyl, cyclopentyl, cyclohexyl or cycloheptyl.

Hal preferably denotes F, Cl or Br, but also 1.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino) phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4, 6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^2$, $NR^2COA$, $SO_2A$, $COOR^2$ or CN. Ar particularly preferably denotes, for example, phenyl which is unsubstituted or mono-, di- or trisubstituted by Hal, A, $OR^3$ or NHCOA, such as, for example, phenyl, o-, m- or p-methylphenyl, o-, m- or p-hydroxyphenyl, o-, m- or p-methoxyphenyl, 2-, 3- or 4-chlorophenyl, 4-bromophenyl, 3-fluoro-4-trifluoromethoxyphenyl, 4-ethoxyphenyl, 3-cyanophenyl, o-, m- or p-acetamidophenyl or 4-ethoxycarbonylphenyl.

Ar very particularly preferably denotes unsubstituted phenyl, 4-chlorophenyl, 4-fluorophenyl, 2,3-difluorophenyl, 2-chlorophenyl, 4-hydroxyphenyl, 2- or 4-methoxyphenyl or 4-acetamidophenyl.

Ar' preferably has the preferred meanings indicated for Ar.

Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or -5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3, 4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated.

Het can thus, for example, also denote 2,3-dihydro-2-, -3-, -4- or -5-furyl, 2,5-dihydro-2-, -3-, 4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)-phenyl or alternatively 3,4-dihydro-2H-1,5-benzodioxepin-6- or -7-yl, furthermore preferably 2,3-dihydrobenzofuranyl or 2,3-dihydro-2-oxo-furanyl.

Het preferably denotes a mono- or bicyclic saturated, unsaturated or aromatic heterocycle having 1 to 2 N, O and/or S atoms, which may be unsubstituted or mono- or disubstituted by carbonyl oxygen, OH or OA. Het preferably denotes, for example, furyl, thienyl, thiazolyl, imidazolyl, 2,1,3-benzothiadiazolyl, oxazolyl, pyridyl, indolyl, piperidinyl, morpholinyl, tetrahydropyranyl, piperazinyl, pyrazinyl, piperidinyl or pyrrolidinyl, optionally substituted by carbonyl oxygen, such as, for example, 3-oxomorpholin-4-yl, 2-oxopiperidin-1-yl or 2-oxopyrrolidin-1-yl.

Het very particularly preferably denotes thienyl, imidazolyl, pyridyl, indolyl, piperidinyl, piperazinyl, 2-oxopiperazinyl, morpholinyl, tetrahydropyran-4-yl, 3-oxomorpholin-4-yl, 2-oxo-2H-pyrazin-1-yl, 2-oxopyrrolidin-1-yl or 2-oxopiperidin-1-yl.

Het' preferably has the preferred meanings indicated for Ar.

D denotes, in particular, for example, phenyl which is unsubstituted or mono- or disubstituted by Hal, A, hydroxyl, methoxy, ethoxy, hydroxycarbonyl, methoxycarbonyl or ethoxycarbonyl, or pyridyl or thienyl, each of which is unsubstituted or monosubstituted by Hal.

D very particularly preferably denotes 4-chlorophenyl.

$R^1$ preferably denotes Ar, such as, for example, phenyl, o-, m- or p-fluorophenyl, o-, m- or p-chlorophenyl, o-, m- or p-hydroxyphenyl, o-, m- or p-methoxyphenyl or difluorophenyl; Het, such as, for example, thienyl or furyl; cycloalkyl, such as, for example, cyclohexyl; or A, which may be monosubstituted by $OR^2$, such as, for example, methyl, ethyl, propyl, butyl, —$CH(CH_3)OH$ or —$CH(CH_3)OCH_3$.

$R^1$ particularly preferably denotes phenyl which is unsubstituted or mono-, di- or trisubstituted by Hal, OH or OA, such as, for example, phenyl, o-, m- or p-fluorophenyl, o-, m- or p-chlorophenyl, o-, m- or p-hydroxyphenyl, o-, m- or p-methoxyphenyl, difluorophenyl or trifluorophenyl; a monocyclic aromatic heterocycle having 1 to 2 N, O and/or S atoms, such as, for example, thienyl or furyl; or A, which may be monosubstituted by $OR^3$, such as, for example, methyl, ethyl, propyl, butyl, —$CH(CH_3)OH$ or —$CH(CH_3)OCH_3$.

$R^1$ preferably denotes, for example, H or alkyl having 1, 2, 3, 4, 5 or 6 C atoms, very particularly preferably H.

$R^3$ preferably denotes, for example, H or alkyl having 1, 2, 3, 4, 5 or 6 C atoms, very particularly preferably H.

$R^4$, $R^{4'}$ preferably denote A, OH, OA or are absent; together also methylene or ethylene. $R^4$, $R^{4'}$ particularly preferably denote "absent".

T preferably denotes a mono- or bicyclic saturated, unsaturated or aromatic heterocycle having 1 to 2 N, O and/or S atoms, which may be unsubstituted or mono- or disubstituted by A or carbonyl oxygen (=O), phenyl which is unsubstituted or mono-, di- or trisubstituted by Hal, $OR^2$ or $NR^2COA$, or a monocyclic unsubstituted, saturated carbocycle.

The unsubstituted saturated carbocycle preferably denotes cyclopentyl or cyclohexyl.

T particularly preferably denotes a monocyclic saturated or aromatic heterocycle having 1 to 2 N and/or O atoms, which may be unsubstituted or mono- or disubstituted by A or carbonyl oxygen (=O), phenyl which is unsubstituted or mono-, di- or trisubstituted by Hal, OH, OA or NHCOA, or a monocyclic unsubstituted, saturated carbocycle.

T denotes, in particular, piperidinyl, piperazinyl, pyridinyl, 2-oxopiperidin-1-yl, 2-oxopiperidin-4-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperidin1-yl, 2-oxopiperazin-1-yl, 2,6-dioxopiperazin-1-yl, 2,5-dioxopyrrolidin-1-yl, 2-oxo-1,3-oxazolidin-3-yl, pyridazinyl, 3-oxo-2H-pyridazin-2-yl, 2-caprolactam-1-yl (=2-oxoazepan-1-yl), 6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, where the radicals may additionally be monosubstituted by A, phenyl which is unsubstituted or mono-, di- or trisubstituted by Hal, OH, OA or NHCOA, or a monocyclic unsubstituted, saturated carbocycle.

T piperidin-1- or 4-yl, piperazinyl, morpholin-4-yl, each of which is unsubstituted or monosubstituted by A and/or carbonyl oxygen (=O), or unsubstituted cyclohexyl, In a particularly preferred embodiment, $R^4$, $R^{4'}$ is absent, Z, Z' each denote ethylene, E denotes CH or N, T denotes piperidin-1- or 4-yl, piperazinyl, 2-oxopiperazin-1-yl, morpholin-4-yl, each of which is unsubstituted or monosubstituted by A, or unsubstituted cyclohexyl.

The compounds of the formula I may have one or more chiral centres and therefore occur in various stereoisomeric forms. The formula I covers all these forms.

Accordingly, the invention relates, in particular, to the compounds of the formula I in which at least one of the said radicals has one of the preferred meanings indicated above. Some preferred groups of compounds may be expressed by the following sub-formulae Ia to Is, which conform to the formula I and in which the radicals not designated in greater detail have the meaning indicated under the formula I, but in which in Ia D denotes phenyl which is unsubstituted or mono- or disubstituted by Hal, A, $OR^2$ or $COOR^2$, or pyridyl which is unsubstituted or monosubstituted by Hal;

in Ib D denotes phenyl which is monosubstituted by Hal;

in Ic $R^2$ denotes H or A;

in Id T denotes a mono- or bicyclic saturated, unsaturated or aromatic heterocycle having 1 to 2 N, O and/or S atoms, which may be unsubstituted or mono- or disubstituted by A or carbonyl oxygen (=O),
  phenyl which is unsubstituted or mono-, di- or trisubstituted by Hal, $OR^2$ or $NR^2COA$,
  or a monocyclic unsubstituted, saturated carbocycle;
in Ie Q is absent or denotes O or $CH_2$;
in If Ar denotes phenyl which is unsubstituted or mono-, di- or trisubstituted by Hal, A, $OR^2$, $NR^2COA$, $SO_2A$, $SO_2NH_2$, $COOR^2$ or CN;
in Ig Ar denotes phenyl which is unsubstituted or mono-, di- or trisubstituted by Hal, A, $OR^3$ or $NR^3COA$;
in Ih $R^1$ denotes Ar, Het, cycloalkyl or
  A, which may be monosubstituted by $OR^2$;
in Ii $R^1$ denotes phenyl which is unsubstituted or mono-, di- or trisubstituted by Hal, OH or OA,
  a monocyclic aromatic heterocycle having 1 to 2 N, O and/or S atoms,
  or
  A, which may be monosubstituted by $OR^3$;
in Ij Het denotes a mono- or bicyclic saturated, unsaturated or aromatic heterocycle having 1 to 2 N, O and/or S atoms, which may be unsubstituted or mono- or disubstituted by A or carbonyl oxygen (=O),
in Ik Y denotes O;
in Il X denotes $NR^{3'}$ or O,
  $R^{3'}$ denotes H;
in Im Z, Z' denote ethylene;
in In T denote a monocyclic saturated or aromatic heterocycle having 1 to 2 N and/or O atoms, which may be unsubstituted or mono- or disubstituted by A or carbonyl oxygen (=O),
  phenyl which is unsubstituted or mono-, di- or trisubstituted by Hal, OH, OA or NHCOA,
  or a monocyclic unsubstituted, saturated carbocycle;
in Io A denotes unbranched or branched alkyl having 1-10 C atoms, in which 1-7 H atoms may be replaced by F;
in Ip D denotes phenyl which is unsubstituted or mono- or disubstituted by Hal, A, $OR^2$ or $COOR^2$, or pyridyl which is unsubstituted or monosubstituted by Hal,
  X denotes $NR^3$ or O,
  Y denotes O,
  $R^1$ denotes Ar, Het, cycloalkyl or
    A, which may be monosubstituted by $OR^2$,
  E denotes CH or N,
  Z, Z' denote ethylene,
  Q is absent or denotes O or $CH_2$,
  $R^2$ denotes H or A,
  $R^3$ denotes H or A,
  $R^4$, $R^{4'}$ each, independently of one another, is absent or denote A, OH or OA,
  $R^4$ and $R^{4'}$ together also denote methylene or ethylene,
  T denotes a monocyclic saturated or aromatic heterocycle having 1 to 2 N and/or O atoms, which may be unsubstituted or mono- or disubstituted by A or carbonyl oxygen (=O),
    phenyl which is unsubstituted or mono-, di- or trisubstituted by Hal, OH, OA or NHCOA,
    or a monocyclic unsubstituted, saturated carbocycle,
  A denotes unbranched or branched alkyl having 1-10 C atoms, in which 1-7 H atoms may be replaced by F,
  Ar denotes phenyl which is unsubstituted or mono-, di- or trisubstituted by Hal, A, $OR^2$, $NR^2COA$, $SO_2A$, $SO_2NH_2$, $COOR^2$ or CN,
  Het denotes a mono- or bicyclic saturated, unsaturated or aromatic heterocycle having 1 to 2 N, O and/or S atoms, which may be unsubstituted or mono- or disubstituted by A or carbonyl oxygen (=O),
  Hal denotes F, Cl, Br or I,
  p denotes 1, 2, 3, 4 or 5;
in Iq D denotes phenyl which is monosubstituted by Hal,
  X denotes $NR^{3'}$ or O,
  Y denotes O,
  $R^1$ denotes phenyl which is unsubstituted or mono-, di- or trisubstituted by Hal, OH or OA,
    a monocyclic aromatic heterocycle having 1 to 2 N, O and/or S atoms,
    or
    A, which may be monosubstituted by $OR^3$,
  $R^{3'}$ denotes H,
  E denotes CH or N,
  Z, Z' denote ethylene,
  Q is absent or denotes O or $CH_2$,
  $R^2$ denotes H or A,
  $R^3$ denotes H or A,
  $R^4$, $R^{4'}$ each, independently of one another, is absent or denote A, OH or OA,
  $R^4$ and $R^{4'}$ together also denote methylene or ethylene,
  T denotes a monocyclic saturated or aromatic heterocycle having 1 to 2 N and/or O atoms, which may be unsubstituted or mono- or disubstituted by A or carbonyl oxygen (=O),
    phenyl which is unsubstituted or mono-, di- or trisubstituted by Hal, OH, OA or NHCOA,
    or a monocyclic unsubstituted, saturated carbocycle,
  A denotes unbranched or branched alkyl having 1-10 C atoms, in which 1-7 H atoms may be replaced by F,
  Hal denotes F, Cl, Br or I;
in Ir D denotes phenyl which is monosubstituted by Hal,
  X denotes $NR^{3'}$ or O,
  Y denotes O,
  $R^1$ denotes thienyl, furyl, phenyl which is unsubstituted or mono-, di- or trisubstituted by Hal, OH or OA,
    or
    A, which may be monosubstituted by $OR^3$,
  $R^3$ denotes H or A,
  $R^{3'}$ denotes H,
  E denotes CH or N,
  Z, Z' denote ethylene,
  Q is absent or denotes O or $CH_2$,
  $R^2$ denotes H or A,
  $R^3$ denotes H or A,
  $R^4$, $R^{4'}$ each, independently of one another, is absent or denote A, OH or OA,
  $R^4$ and $R^{4'}$ together also denote methylene or ethylene,
  T denotes piperidinyl, piperazinyl, pyridinyl, 2-oxopiperidin-1-yl, 2-oxopiperidin-4-yl, 2-oxopyrrolidin-1-yl, pyrrolidin-1-yl, 2-oxo-1H-pyridin-1-yl, 3-oxomorpholin-4-yl, morpholin-4-yl, 4-oxo-1H-pyridin-1-yl, 2,6-dioxopiperidin-1-yl, 2-oxo-piperazin-1-yl, 2,6-dioxopiperazin1-yl, 2,5-dioxopyrrolidin-1-yl, 2-oxo-1,3-oxazolidin-3-yl, pyridazinyl, 3-oxo-2H-pyridazin-2-yl, 2-caprolactam-1-yl (=2-oxoazepan-1-yl), 6-oxopiperazin-1-yl, 2-azabicyclo[2.2.2]octan-3-on-2-yl, 5,6-dihydro-1H-pyrimidin-2-oxo-1-yl, 2-oxo-1,3-oxazinan-3-yl or 4H-1,4-oxazin-4-yl, where the radicals may additionally be monosubstituted by A,
    phenyl which is unsubstituted or mono-, di- or trisubstituted by Hal, OH, OA or NHCOA,
    or a monocyclic unsubstituted, saturated carbocycle,
  A denotes unbranched or branched alkyl having 1-10 C atoms, in which 1-7 H atoms may be replaced by F,
  Hal denotes F, Cl, Br or I;
in Is D denotes phenyl which is monosubstituted by Hal,
  X denotes $NR^{3'}$ or O, Y denotes O, R$^1$ denotes thienyl, furyl, phenyl which is unsubstituted or mono-, di- or trisubstituted by Hal, OH or OA, or A, which may be monosubstituted by OR$^3$ R$^3$ denotes H or A, R$^{3'}$ denotes H, E denotes CH or N, Z denotes ethylene, Z' denotes ethylene, Q is absent or denotes O or CH$_2$, R$^2$ denotes H or A, R$^3$ denotes H or A, R$^4$, R$^{4'}$ is absent, R$^4$ and R$^{4'}$ together also denote methylene or ethylene, T denotes piperidin-1- or 4-yl, piperazinyl or morpholin-4-yl, each of which is unsubstituted or monosubstituted by A and/or carbonyl oxygen (=O), or unsubstituted cyclohexyl, A denotes unbranched or branched alkyl having 1-10 C atoms, in which 1-7 H atoms may be replaced by F, Hal denotes F, Cl, Br or I;

and pharmaceutically usable derivatives, solvates and stereoisomers thereof, including mixtures thereof in all ratios.

The compounds of the formula I and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

If desired, the starting materials can also be formed in situ so that they are not isolated from the reaction mixture, but instead are immediately converted further into the compounds of the formula I.

Compounds of the formula I in which

X denotes NH and

Y denotes O, can preferably be obtained by reacting compounds of the formula II with compounds of the formula III.

The reaction is generally carried out in an inert solvent, optionally in the presence of an organic base, such as triethylamine, dimethylaniline, pyridine or quinoline. Depending on the conditions used, the reaction time is between a few minutes and 14 days, preferably between one and ten hours, the reaction temperature is between about 0° and 150°, normally between 10° and 130°, preferably between 10° and 90°, very particularly preferably between 20° and 80° C.

Examples of suitable inert solvents are water; hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The starting compounds of the formulae II and III are generally known. If they are novel, they can, however, be prepared by methods known per se.

Compounds of the formula I in which X and Y denote O can also be obtained by reacting compounds of the formula IV with compounds of the formula V.

In the compounds of the formula V, L preferably denotes Cl, Br, I or a reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethylaniline, pyridine or quinoline, or an excess of the amine component of the formula IV may also be favourable. Depending on the conditions used, the reaction time is between a few minutes and 14 days, the reaction temperature is between about 0° and 150°, normally between 20° and 130°. Suitable inert solvents are those mentioned above.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as (C$_1$-C$_4$)alkyl halides, for example methyl, ethyl, isopropyl and tert-butyl chloride, bromide and iodide; di(C$_1$-C$_4$) alkyl sulfates, for example dimethyl, diethyl and diamyl sulfate; (C$_{10}$-C$_{18}$)alkyl halides, for example decyl, dodecyl, lauryl, myristyl and stearyl chloride, bromide and iodide; and aryl(C$_1$-C$_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form provides the active ingredient with improved pharmacokinetic properties compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of pharmaceutical compositions, in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal anti-bodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, poly-dihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in the freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment.

The compounds of the formula I and physiologically acceptable salts thereof can be used for combating and preventing thromboembolic diseases, such as thrombosis, myocardial infarction, arteriosclerosis, inflammation, apoplexy, angina pectoris, restenosis after angioplasty, claudicatio intermittens, migraine, tumours, tumour diseases and/or tumour metastases.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The invention furthermore relates to the use of compounds of the formula I and/or pharmaceutically usable derivatives, solvates and stereoisomers thereof, including mixtures thereof in all ratios,
for the preparation of a medicament for the treatment of thromboses, myocardial infarction, arteriosclerosis, inflammation, apoplexy, angina pectoris, restenosis after angioplasty, claudicatio intermittens, migraine, tumours, tumour diseases and/or tumour metastases, in combination with at least one further medicament active ingredient.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M⁺

ESI (electrospray ionisation) (M+H)⁺

FAB (fast atom bombardment) (M+H)⁺

EXAMPLE 1

The preparation of (R)-1-(4-chlorophenyl)-3-[2-(1'-methyl-4,4'-bipiperidinyl-1-yl)-2-oxo-1-phenylethyl]urea (1) is carried out analogously to the following scheme:

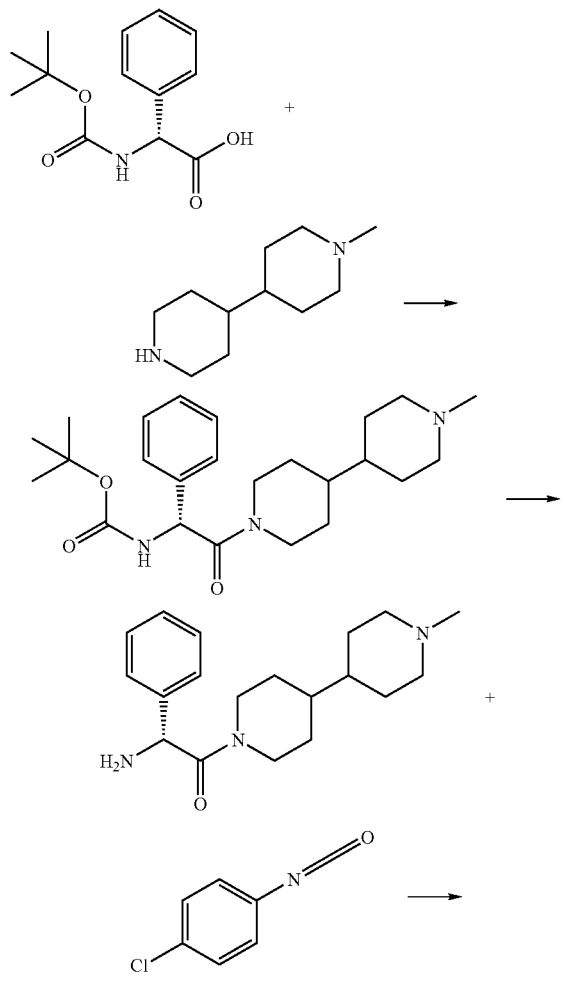

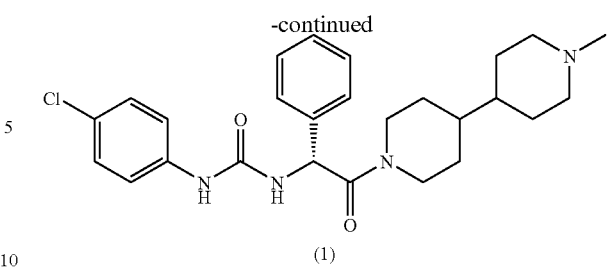

1.1 Preparation of tert-butyl(R)-[2-(1'-methyl-4,4'-bipiperidinyl-1-yl)-2-oxo-1-phenylethyl]carbamate 3.28 g (11.06 mmol) of 1-methyl-4,4'-bipiperidinyl are dissolved in 30 ml of dimethylformamide together with 2.78 g (11.06 mmol) of (R)-Boc-phenylglycine, 2.33 g (12.17 mmol) of (N-(3-dimethylaminopropyl)-N'-ethylcarbodiimide hydrochloride (DAPECI) and 1.86 g (12.17 mmol) of hydroxybenzotriazole hydrate, and 4 ml of 4-methylmorpholine are added. After 24 hours, the reaction mixture is subjected to conventional work-up, giving 1.8 g of tert-butyl(R)-[2-(1'-methyl-4,4'-bipiperidinyl-1-yl)-2-oxo-1-phenylethyl] carbamate.

1.2 Preparation of N-(1'-methyl-4,4'-bipiperidinyl-1-yl)-(R)-2-amino-2-phenylacetamide trifluoroacetate 1.8 g (4.33 mmol) of tert-butyl(R)-[2-(1'-methyl-4,4'-bipiperidinyl-1-yl)-2-oxo-1-phenylethyl]carbamate are dissolved in 30 ml of 20% trifluoroacetic acid in dichloromethane, and the mixture is stirred for 2 hours. Work-up gives N-(1'-methyl-4,4'-bipiperidinyl-1-yl)-(R)-2-amino-2-phenylacetamide trifluoroacetate quantitatively.

1.3 0.93 g (1.02 mmol) of N-(1'-methyl-4,4'-bipiperidinyl-1-yl)-(R)-2-amino-2-phenylacetamide trifluoroacetate are dissolved in 50 ml of dichloromethane together with 165 mg (1.07 mmol) of 4-chlorophenyl isocyanate with addition of 0.9 ml of triethylamine, and the mixture is stirred for 24 h. Conventional work-up and chromatography gives 250 mg of (R)-1-(4-chlorophenyl)-3-[2-(1'-methyl-4,4'-bipiperidinyl-1-yl)-2-oxo-1-phenylethyl]urea (1), ESI 470.

The following compounds are obtained analogously (R)-1-(4-chlorophenyl)-3-{2-[4-(4-fluorophenyl)piperazin-1-yl]-2-oxo-1-phenylethyl}urea (2), ESI 467;

(R)-1-(4-chlorophenyl)-3-{2-[4-(4-fluorophenoxy)piperidin-1-yl]-2-oxo-1-phenylethyl}urea (3), ESI 482;

(R)-1-(4-chlorophenyl)-3-[2-oxo-1-phenyl-2-(4-pyridin-4-ylpiperazin-1-yl)ethyl]urea bistrifluoroacetate (4), ESI 450;

(R)-1-(4-chlorophenyl)-3-{2-[4-(1-methylpiperidin-4-yl)piperazin-1-yl]-2-oxo-1-phenylethyl}urea bistrifluoroacetate (5), ESI471;

(R)-1-(4-chlorophenyl)-3-{2-[4-(4-ethylpiperazin-1-yl)piperidin-1-yl]-2-oxo-1-phenylethyl}urea bistrifluoroacetate (6), ESI 485;

(R)-1-(4-chlorophenyl)-3-[2-oxo-1-phenyl-2-(4-pyridin-3-ylmethyl-piperazin-1-yl)ethyl]urea bistrifluoroacetate (7), ESI 464;

(R,S)-1-(4-chlorophenyl)-3-{2-methoxy-1-[1-(4-pyridin-4-yl piperazin-1-yl)methanoyl]propyl}urea bistrifluoroacetate (8), ESI 432;

(R,S)-1-(4-chlorophenyl)-3-(2-methoxy-1-{1-[4-(1-methylpiperidin-4-yl)piperazin-1-yl]methanoyl}propyl)urea bistrifluoroacetate (9), ESI 453

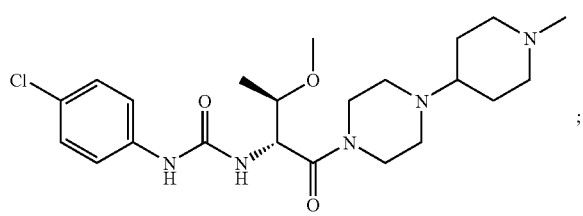

(R,S)-1-(4-chlorophenyl)-3-{2-methoxy-1-[1-(1'-methyl-4,4'-bipiperidinyl-1-yl)methanoyl]propyl}urea trifluoroacetate (10), ESI 452;
(R)-1-(4-chlorophenyl)-3-[2-oxo-1-phenyl-2-(4-pyridin-4-ylpiperazin-1-yl)ethyl]urea (11), ESI 450;
(R)-1-(4-chlorophenyl)-3-[1-(4-pyridin-4-ylpiperazine-1-carbonyl)butyl]urea (12), ESI 416;
(R)-1-(4-chlorophenyl)-3-{2-[4-hydroxy-4-(4-methoxyphenyl)piperidin-1-yl]-2-oxo-1-phenylethyl}urea (13), ESI 477;
(R)-1-(4-chlorophenyl)-3-{2-[4-(2-methoxyphenyl)piperazin-1-yl]-2-oxo-1-phenylethyl}urea (14), ESI 479;
(R)—N-[4-(1-{2-[3-(4-chlorophenyl)ureido]-2-phenylethanoyl}piperidin-4-ylmethyl)phenyl]acetamide (15), ESI 510;
(R)-1-(4-chlorophenyl)-3-{2-oxo-1-phenyl-2-[4-(1-phenylmethanoyl)piperidin-1-yl]ethyl}urea (16); ESI 476;
(R)-1-(4-chlorophenyl)-3-[2-oxo-1-phenyl-2-(4-pyridin-2-ylpiperazin-1-yl)ethyl]urea (17), ESI 450;
(R)-1-[2-(4-benzylpiperazin-1-yl)-2-oxo-1-phenylethyl]-3-(4-chlorophenyl)urea (18), ESI 463;
(R)-1-(4-chlorophenyl)-3-{2-[5-(4-fluorophenyl)-2,5-diazabicyclo-[2.2.1]hept-2-yl]-2-oxo-1-phenylethyl}urea (19), ESI 479

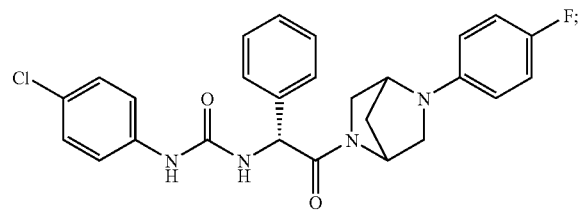

(R)-1-(4-chlorophenyl)-3-{2-[4-(4,6-dimethylpyrimidin-2-yl)piperazin-1-yl]-2-oxo-1-phenylethyl}urea (20), ESI 479;
(R,S)-1-[2-(3-benzylpiperidin-1-yl)-2-oxo-1-phenylethyl]-3-(4-chlorophenyl)urea (21), ESI 463;
(S,S)-1-(4-chlorophenyl)-3-{2-hydroxy-1-[1-(4-pyridin-4-ylpiperazin-1-yl)methanoyl]propyl}urea (22), ESI 418;
(S,S)-1-(4-chlorophenyl)-3-(2-hydroxy-1-{1-[4-(1-methylpiperidin-4-yl)piperazin-1-yl]methanoyl}propyl)urea (23), ESI 438;
(R,R)-1-(4-chlorophenyl)-3-{2-methoxy-1-[1-(4-pyridin-3-ylmethyl-piperazin-1-yl)methanoyl]propyl}urea bistrifluoroacetate (24), ESI 446;
(R)-1-(4-chlorophenyl)-3-[2-oxo-1-phenyl-2-(4-pyridin-4-ylpiperazin-1-yl)ethyl]urea bistrifluoroacetate (25), ESI 450;
(R,R)-1-(4-chlorophenyl)-3-(1-{1-[4-(4-ethylpiperazin-1-yl)piperidin-1-yl]methanoyl}-2-methoxypropyl)urea bistrifluoroacetate (26), ESI 467;
(R)-1-(4-chlorophenyl)-3-{2-[4-(1-methylpiperidin-4-yl)piperazin-1-yl]-2-oxo-1-phenylethyl}urea bistrifluoroacetate (27), ESI 471;

(R)-1-(2-4,4'-bipiperidinyl-1-yl-2-oxo-1-phenylethyl)-3-(4-chlorophenyl)urea hydrochloride (28), ESI 456;
(R)-1-[2-4,4'-bipiperidinyl-1-yl-1-(4-hydroxyphenyl)-2-oxoethyl]-3-(4-chlorophenyl)urea hydrochloride (29), ESI 472;
(R)-1-(2-4,4'-bipiperidinyl-1-yl-2-oxo-1-thiophen-2-ylethyl)-3-(4-chlorophenyl)urea hydrochloride (30), ESI 462;
(R)-1-(4-chlorophenyl)-3-[1-(4-hydroxyphenyl)-2-(1'-methyl-4,4'-bipiperidinyl-1-yl)-2-oxoethyl]urea trifluoroacetate (31), ESI 486;
(R)-1-(4-chlorophenyl)-3-[2-(1'-methyl-4,4'-bipiperidinyl-1-yl)-2-oxo-1-thiophen-2-ylethyl]urea trifluoroacetate (32), ESI 476;
(R)-1-(4-chlorophenyl)-3-[1-(4-hydroxyphenyl)-2-(4-morpholin-4-yl-piperidin-1-yl)-2-oxoethyl]urea trifluoroacetate (33), ESI 473;
1-[2-[1,4']bipiperidinyl-1'-yl-1-(4-hydroxyphenyl)-2-oxoethyl]-3-(4-chlorophenyl)urea,
(R)-1-(4-chlorophenyl)-3-[2-(4-morpholin-4-ylpiperidin-1-yl)-2-oxo-1-phenylethyl]urea trifluoroacetate (35), ESI 457;
(R)-1-(2-[1,4']bipiperidinyl-1'-yl-2-oxo-1-phenylethyl)-3-(4-chlorophenyl)urea trifluoroacetate (36), ESI 456;
(R)-1-(4-chlorophenyl)-3-[2-(4-cyclohexylpiperazin-1-yl)-1-(4-hydroxyphenyl)-2-oxoethyl]urea trifluoroacetate (37), ESI 471;
(R)-1-(4-chlorophenyl)-3-[2-(4-cyclohexylpiperazin-1-yl)-2-oxo-1-phenylethyl]urea trifluoroacetate (38), ESI 456;
(R)-1-(4-chlorophenyl)-3-{1-(4-hydroxyphenyl)-2-[4-(4-methylpiperazin-1-yl)piperidin-1-yl]-2-oxoethyl}urea bistrifluoroacetate (39), ESI 487;
(R)-1-(4-chlorophenyl)-3-{2-[4-(4-methylpiperazin-1-yl)piperidin-1-yl]-2-oxo-1-phenylethyl}urea bistrifluoroacetate (40), ESI 471;
(R)-1-(4-chlorophenyl)-3-[2-(4-morpholin-4-ylpiperidin-1-yl)-2-oxo-1-thiophen-2-ylethyl]urea trifluoroacetate (41), ESI 464;
(R)-1-(2-[1,4']bipiperidinyl-1'-yl-2-oxo-1-thiophen-2-ylethyl)-3-(4-chlorophenyl)urea trifluoroacetate (42), ESI 462;
(R)-1-(4-chlorophenyl)-3-[2-(4-cyclohexylpiperazin-1-yl)-2-oxo-1-thiophen-2-ylethyl]urea trifluoroacetate (43), ESI 462;
(R)-1-(4-chlorophenyl)-3-{2-[4-(4-methylpiperazin-1-yl)piperidin-1-yl]-2-oxo-1-thiophen-2-ylethyl}urea bistrifluoroacetate (44), ESI 477;
(R)-1-(4-chlorophenyl)-3-[2-(1'-methyl-4,4'-bipiperidinyl-1-yl)-2-oxo-1-(2-chlorophenyl)ethyl]urea (45),
(R)-1-(4-chlorophenyl)-3-[2-(4,4'-bipiperidinyl-1-yl)-2-oxo-1-(2-chlorophenyl)ethyl]urea (46),
(R)-1-(4-chlorophenyl)-3-[1-(2-chlorophenyl)-2-(1'-methyl-2'-oxo-4,4'-bipiperidinyl-1-yl)-2-oxoethyl]urea (47)

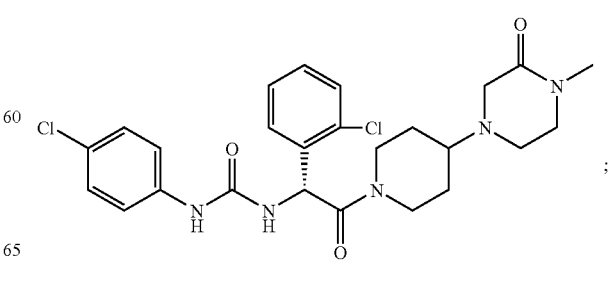

(R)-1-(4-chlorophenyl)-3-[1-phenyl-2-(1'-methyl-2'-oxo-4,4'-bipiperidinyl-1-yl)-2-oxoethyl]urea (48).

EXAMPLE 2

The preparation of 2-(1'-methyl-4,4'-bipiperidinyl-1-yl)-2-oxo-1-phenylethyl (R)-4-chlorophenyl)carbamate (49) is carried out analogously to the following scheme:

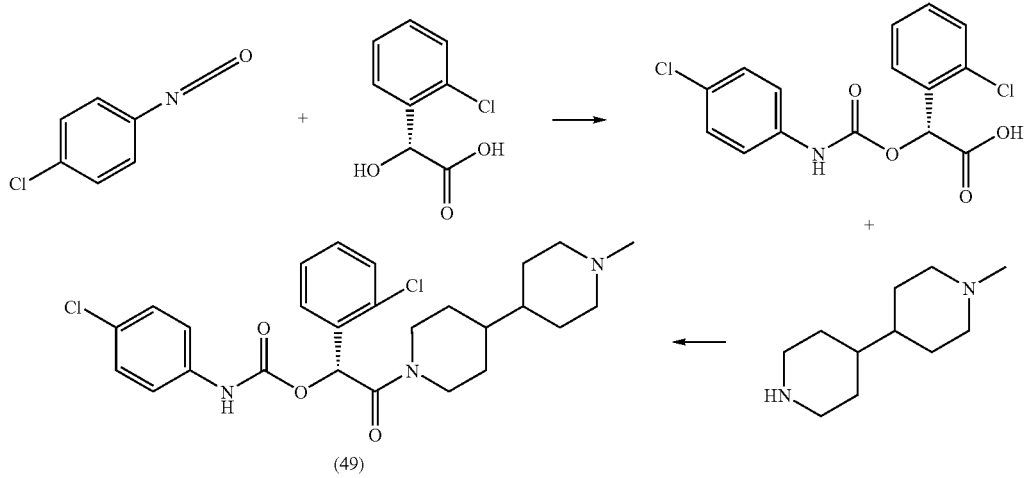

(49)

2.1 Preparation of (R)-(2-chlorophenyl)(4-chlorophenylcarbamoyloxy)-acetic acid 1 g (5 mmol) of (R)-(2-chlorophenyl)hydroxyacetic acid are dissolved in 10 ml of dichloromethane, and 0.77 g (5 mmol) of 4-chlorophenyl isocyanate and 50 mg of dibutyltin dilaurate are added successively, and the mixture is stirred for 16 hours. Conventional work-up gives 1.5 g of (R)-(2-chlorophenyl)(4-chlorophenylcarbamoyloxy)acetic acid.

2.2 92 mg (0.5 mmol) of 1-methyl-4,4'-bipiperidinyl are dissolved in 2 ml of dimethylformamide together with 170 mg (0.5 mmol) of (R)-(2-chlorophenyl)-(4-chlorophenylcarbamoyloxy)acetic acid, 124 mg (0.65 mmol) of (N-(3-dimethylaminepropyl)-N'-ethylcarbodiimide hydrochloride (DAPECI) and 100 mg (0.65 mmol) of hydroxybenzotriazole hydrate, and 72 μl of 4-methylmorpholine are added. After 24 hours, the reaction mixture is subjected to conventional work-up. Chromatography gives 15 mg of 2-(1'-methyl-4,4'-bipiperidinyl-1-yl)-2-oxo-1-phenylethyl (R)-4-chlorophenyl)carbamate trifluoroacetate (49), ESI 471.

The following compounds are obtained analogously
2-oxo-1-phenyl-2-(4-pyridin-4-ylpiperazin-1-yl)ethyl(R)-(4-chlorophenyl)carbamate (50), ESI 451;
2-4,4'-bipiperidinyl-1-yl-1-(2-chlorophenyl)-2-oxoethyl(R)-(4-chlorophenyl) carbamate hydrochloride (51), ESI 491;
2-4,4'-bipiperidinyl-1-yl-2-oxo-1-phenylethyl(R)-(4-chlorophenyl)carbamate hydrochloride (52), ESI 456;
1-(2-chlorophenyl)-2-(1'-methyl-4,4'-bipiperidinyl-1-yl)-2-oxoethyl (R)-(4-chlorophenyl)carbamate trifluoroacetate (53), ESI 505;
1-(2-chlorophenyl)-2-(4-morpholin-4-ylpiperidin-1-yl)-2-oxoethyl (R)-(4-chlorophenyl )carbamate trifluoroacetate (54), ESI 493;
2-[1,4']bipiperidinyl-1'-yl-1-(2-chlorophenyl)-2-oxoethyl (R)-(4-chlorophenyl)carbamate trifluoroacetate (55), ESI 491;
2-(4-morpholin-4-ylpiperidin-1-yl)-2-oxo-1-phenylethyl (R)-(4-chlorophenyl)carbamate trifluoroacetate (56), ESI 458;
2-[1,4']bipiperidinyl-1'-yl-2-oxo-1-phenylethyl(R)-(4-chlorophenyl)carbamate trifluoroacetate (57), ESI 456;
1-(2-chlorophenyl)-2-(4-cyclohexylpiperazin-1-yl)-2-oxoethyl(R)-(4-chlorophenyl)carbamate trifluoroacetate (58), ESI 491;
2-(4-cyclohexylpiperazin-1-yl)-2-oxo-1-phenylethyl(R)-(4-chlorophenyl)carbamate trifluoroacetate (59), ESI 456;
1-(2-chlorophenyl)-2-[4-(4-methylpiperazin-1-yl)piperidin-1-yl]-2-oxoethyl(R)-(4-chlorophenyl)carbamate bistrifluoroacetate (60), ESI 506;
2-[4-(4-methylpiperazin-1-yl)piperidin-1-yl]-2-oxo-1-phenylethyl(R)-(4-chlorophenyl)carbamate bistrifluoroacetate (61), ESI 472;
1-(2,3-difluorophenyl)-2-(1'-methyl-4,4'-bipiperidinyl-1-yl )-2-oxoethyl (R)-(4-chlorophenyl)carbamate (62), ESI 507;
1-(2-fluorophenyl)-2-(1'-methyl-4,4'-bipiperidinyl-1-yl)-2-oxoethyl(R)-(4-chlorophenyl)carbamate (63), ESI 489:
1-(2-methoxyphenyl )-2-(1'-methyl-4,4'-bipiperidinyl-1-yl )-2-oxoethyl (R)-(4-chlorophenyl)carbamate (64), ESI 501.

Pharmacological Data (Affinity to Receptors)

| Compound No. | FXa-IC$_{50}$ [M] | TF/FVIIa-IC$_{50}$ [M] |
| --- | --- | --- |
| 1 | $6 \times 10^{-9}$ | $6.9 \times 10^{-9}$ |
| 2 | $6.7 \times 10^{-7}$ | $1.7 \times 10^{-6}$ |
| 5 | $1.7 \times 10^{-8}$ | $6.3 \times 10^{-9}$ |
| 49 | $1.1 \times 10^{-8}$ | $1.5 \times 10^{-8}$ |

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula I

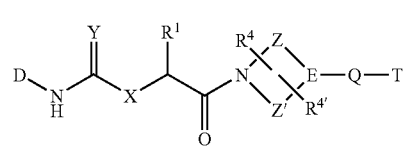

in which
D is phenyl which is unsubstituted or mono- or polysubstituted by Hal, A, $OR^2$, $N(R^2)_2$, $NO_2$, CN, $COOR^2$, $CON(R^2)_2$ or —C≡CH,
X denotes $NR^3$ or O,
Y denotes O, S, NH, N—CN or N—$NO_2$,
$R^1$ denotes H, Ar, Het, or cycloalkyl,
$R^1$ may also be A which is optionally mono-, di- or trisubstituted by $OR^2$, $SR^2$, $S(O)_mR^2$, $SO_2N(R^2)_2$, $SO_3R^2$, $S(=O)(=NR^2)R^2$, $NR^2SO_2R^2$, $OSO_2R^2$, $OSO_2N(R^2)_2$, $N(R^2)_2$, CN, $COOR^2$, $CON(R^2)_2$, Ar, Het or cycloalkyl,
E denotes CH,
Z is ethylene,
Z' is ethylene,
Q is absent or denotes O, $NR^2$, C=O, $SO_2$ or $C(R^2)_2$,
$R^2$ denotes H, A, —$[C(R^3)_2]_n$—Ar', —$[C(R^3)_2]_n$-Het', —$[C(R^3)_2]_n$-cycloalkyl, —$[C(R^3)_2]_n$—$N(R^3)_2$ or —$[C(R^3)_2]_n$—$OR^3$,
$R^3$ denotes H or A,
$R^4$, $R^{4'}$ each, independently of one another, is absent or denote A, OH or OA, or $R^4$ and $R^{4'}$ together denote methylene or ethylene,
T is cyclohexyl, piperidinyl, piperazinyl, or morpholinyl, which in each case is optionally mono-, di- or trisubstituted by =O, =S, =NH, =$NR^3$, =$NOR^3$, =$NCOR^3$, =$NCOOR^3$, =$NOCOR^3$, $R^3$, Hal, A, —$[C(R^3)_2]_n$—Ar, —$[C(R^3)_2]_n$-Het, —$[C(R^3)_2]_n$—cycloalkyl, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2NR^2$ and/or $S(O)_nA$,
A denotes unbranched or branched alkyl having 1-10 C atoms, in which one or two $CH_2$ groups may be replaced by O or S atoms and/or by —CH=CH— groups and/or also 1-7 H atoms may be replaced by F,
Ar denotes phenyl, naphthyl or biphenyl, each of which is unsubstituted or mono-, di- or trisubstituted by Hal, A, $OR^2$, $N(R^2)_2$, $NO_2$, CN, $COOR^2$, $CON(R^2)_2$, $NR^2COA$, $NR^2SO_2A$, $COR^2$, $SO_2N(R^2)_2$, —$[C(R^3)_2]_n$—$COOR^2$, —O—$[C(R^3)_2]_o$—$COOR^2$, $SO_3H$ or $S(O)_nA$,
Ar' denotes phenyl which is unsubstituted or mono-, di- or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_nA$, —$[C(R^3)_2]_n$—$COOR^3$ or —O—$[C(R^3)_2]_o$—$COOR^3$,
Het denotes a mono- or bicyclic saturated, unsaturated or aromatic heterocycle having 1 to 4 N, O and/or S atoms, which may be unsubstituted or mono-, di- or trisubstituted by carbonyl oxygen (=O), =S, =$N(R^2)_2$, Hal, A, —$[C(R^3)_2]_n$—Ar, —$[C(R^3)_2]_n$-Het', —$[C(R^3)_2]_n$-cycloalkyl, —$[C(R^3)_2]_n$—$OR^2$, —$[C(R^3)_2]_n$—$N(R^3)_2$, $NO_2$, CN, —$[C(R^3)_2]_n$—$COOR^2$, —$[C(R^3)_2]_n$—$CON(R^2)_2$, —$[C(R^3)_2]_n$—$NR^2COA$, $NR^2CON(R^2)_2$, —$[C(R^3)_2]_n$—$NR^2SO_2A$, $COR^2$, $SO_2N(R^2)_2$ and/or $S(O)_nA$,
Het' denotes a mono- or bicyclic saturated, unsaturated or aromatic heterocycle having 1 to 4 N, O and/or S atoms, which may be unsubstituted or mono- or disubstituted by carbonyl oxygen, =S, =N(R$^3$)$_2$, Hal, A, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$N(R$^3$)$_2$ and/or S(O)$_n$A, Hal denotes F, Cl, Br or I, m denotes 1 or 2, n denotes 0, 1 or 2, o denotes 1, 2 or 3, and p denotes 1, 2, 3, 4 or 5, or a pharmaceutically acceptable salt thereof, or a stereoisomer thereof, including mixtures thereof in all ratios.

2. A compound according to claim 1, in which D denotes phenyl which is unsubstituted or mono- or disubstituted by Hal, A, OR$^2$ or COOR$^2$.

3. A compound according to claim 1, in which D denotes phenyl which is monosubstituted by Hal.

4. A compound according to claim 1, in which R$^2$ denotes H or A.

5. A compound according to claim 1, in which Q is absent or denotes O or CH$_2$.

6. A compound according to claim 1, in which Ar denotes phenyl which is unsubstituted or mono-, di- or trisubstituted by Hal, A, OR$^2$, NR$^2$COA, SO$_2$A, SO$_2$NH$_2$, COOR$^2$ or CN.

7. A compound according to claim 1, according to claim 1 in which Ar denotes phenyl which is unsubstituted or mono-, di- or trisubstituted by Hal, A, OR$^3$ or NR$^3$COA.

8. A compound according to claim 1, in which R$^1$ denotes Ar, Het, cycloalkyl or A, which may be monosubstituted by OR$^2$.

9. A compound according to claim 1, in which R$^1$ denotes phenyl which is unsubstituted or mono-, di- or trisubstituted by Hal, OH or OA, a monocyclic aromatic heterocycle having 1 to 2 N, O and/or S atoms, or A, which may be monosubstituted by OR$^3$.

10. A compound according to claim 1, in which Het denotes a mono- or bicyclic saturated, unsaturated or aromatic heterocycle having 1 to 2 N, O and/or S atoms, which may be unsubstituted or mono- or disubstituted by A or carbonyl oxygen (=O).

11. A compound according to claim 1, in which Y denotes O.

12. A compound according to claim 1, in which X denotes NH or O.

13. A compound according to claim 1, in which A denotes unbranched or branched alkyl having 1-10 C atoms, in which 1-7 H atoms may be replaced by F.

14. A compound according to claim 1, in which

D denotes phenyl which is unsubstituted or mono- or disubstituted by Hal, A, OR$^2$ or COOR$^2$, X denotes NR$^3$ or O, Y denotes O, R$^1$ denotes Ar, Het, cycloalkyl or A, which may be monosubstituted by OR$^2$, E denotes CH, Q is absent or denotes O or CH$_2$, R$^2$ denotes H or A, R$^3$ denotes H or A, R$^4$, R$^{4'}$ each, independently of one another, is absent or denote A, OH or OA, or R$^4$ and R$^{4'}$ together denote methylene or ethylene, T denotes piperidinyl, piperazinyl, or morpholinyl, which may be unsubstituted or mono- or disubstituted by A or carbonyl oxygen (=O), or unsubstituted cyclohexyl, A denotes unbranched or branched alkyl having 1-10 C atoms, in which 1-7 H atoms may be replaced by F, Ar denotes phenyl which is unsubstituted or mono-, di- or trisubstituted by Hal, A, OR$^2$, NR$^2$COA, SO$_2$A, SO$_2$NH$_2$, COOR$^2$ or CN, Het denotes a mono- or bicyclic saturated, unsaturated or aromatic heterocycle having 1 to 2 N, O and/or S atoms, which may be unsubstituted or mono- or disubstituted by A or carbonyl oxygen (=O), Hal denotes F, Cl, Br or I, and p denotes 1, 2, 3, 4 or 5.

15. A compound according to claim 1, in which

D denotes phenyl which is monosubstituted by Hal,

X denotes NH or O,

Y denotes O,

R$^1$ denotes phenyl which is unsubstituted or mono-, di- or trisubstituted by Hal, OH or OA, a monocyclic aromatic heterocycle having 1 to 2 N, O and/or S atoms, or A, which may be monosubstituted by OR$^3$, E denotes CH, Q is absent or denotes O or CH$_2$, R$^2$ denotes H or A, R$^3$ denotes H or A, R$^4$, R$^{4'}$ each, independently of one another, is absent or denote A, OH or OA, or R$^4$ and R$^{4'}$ together denote methylene or ethylene, T denotes piperidinyl, piperazinyl, or morpholinyl, which may be unsubstituted or mono- or disubstituted by A or carbonyl oxygen (=O), or phenyl which is unsubstituted or mono-, di- or trisubstituted by Hal, OH, OA or NHCOA, or unsubstituted cyclohexyl, A denotes unbranched or branched alkyl having 1-10 C atoms, in which 1-7 H atoms may be replaced by F, and Hal denotes F, Cl, Br or I.

16. A compound according to claim 1, in which

D denotes phenyl which is monosubstituted by Hal,

X denotes NH or O,

Y denotes O,

R$^1$ denotes thienyl, furyl, phenyl which is unsubstituted or mono-, di- or trisubstituted by Hal, OH or OA, or A, which may be monosubstituted by OR$^3$, R$^3$ denotes H or A, E denotes CH, Q is absent or denotes O or CH$_2$, R$^2$ denotes H or A, R$^3$ denotes H or A, R$^4$, R$^{4'}$ each, independently of one another, is absent or denote A, OH or OA, or R$^4$ and R$^{4'}$ together denote methylene or ethylene, T denotes piperidinyl, piperazinyl, 2-oxopiperidin-1-yl, 2-oxopiperidin-4-yl, 3-oxomorpholin-4-yl, morpholin-4-yl, 2,6-dioxopiperidin-1-yl, or 2-oxo-piperazin-1-yl, 2,6-dioxopiperazin1-yl, which in each case is optionally monosubstituted by A, or unsubstituted cyclohexyl, A denotes unbranched or branched alkyl having 1-10 C atoms, in which 1-7 H atoms may be replaced by F, and Hal denotes F, Cl, Br or I.

17. A compound according to claim 1, in which

D denotes phenyl which is monosubstituted by Hal,

X denotes NH or O,

Y denotes O,

R$^1$ denotes thienyl, furyl, phenyl which is unsubstituted or mono-, di- or trisubstituted by Hal, OH or OA, or A, which may be monosubstituted by OR$^3$, R³ denotes H or A,
E denotes CH,
Q is absent or denotes O or CH₂,
R² denotes H or A,
R³ denotes H or A,
R⁴, R⁴' is absent, or R⁴ and R⁴' together denote methylene or ethylene,
T denotes piperidin-1- or 4-yl, piperazinyl, morpholin-4-yl,
  each of which is unsubstituted or monosubstituted by A and/or carbonyl oxygen (=O), or
  unsubstituted cyclohexyl,
A denotes unbranched or branched alkyl having 1-10 C atoms, in which 1-7 H atoms may be replaced by F, and
Hal denotes F, Cl, Br or I.

18. A compound selected from:
(R)-1-(4-chlorophenyl)-3-[2-(1'-methyl-4,4'-bipiperidinyl-1-yl)-2-oxo-1-phenylethyl]-urea,
(R)-1-(4-chlorophenyl)-3-{2-[4-(4-ethylpiperazin-1-yl)piperidin-1-yl]-2-oxo-1-phenylethyl}urea bistrifluoroacetate,
(R,R)-1-(4-chlorophenyl)-3-{2-methoxy-1-[1-(1'-methyl-4,4'-bipiperidinyl-1-yl)-methanoyl]propyl}urea trifluoroacetate,
(R,R)-1-(4-chlorophenyl)-3-(1-{1-[4-(4-ethylpiperazin-1-yl)piperidin-1-yl]-methanoyl}-2-methoxypropyl)urea,
(R)-1-(2-4,4'-bipiperidinyl-1-yl-2-oxo-1-phenylethyl)-3-(4-chlorophenyl)urea,
(R)-1-[2-4,4'-bipiperidinyl-1-yl-1-(4-hydroxyphenyl)-2-oxoethyl]-3-(4-chlorophenyl)-urea,
(R)-1-(2-4,4'-bipiperidinyl-1-yl-2-oxo-1-thiophen-2-ylethyl)-3-(4-chlorophenyl)urea,
(R)-1-(4-chlorophenyl)-3-[1-(4-hydroxyphenyl)-2-(1'-methyl-4,4'-bipiperidinyl-1-yl)-2-oxoethyl]urea,
(R)-1-(4-chlorophenyl)-3-[2-(1'-methyl-4,4'-bipiperidinyl-1-yl)-2-oxo-1-thiophen-2-ylethyl]urea,
(R)-1-(4-chlorophenyl)-3-[1-(4-hydroxyphenyl)-2-(4-morpholin-4-ylpiperidin-1-yl)-2-oxoethyl]urea,
1-[2-[1,4']bipiperidinyl-1'-yl-1-(4-hydroxyphenyl)-2-oxoethyl]-3-(4-chlorophenyl)-urea,
(R)-1-(4-chlorophenyl)-3-[2-(4-morpholin-4-ylpiperidin-1-yl)-2-oxo-1-phenylethyl]-urea,
(R)-1-(2-[1,4']bipiperidinyl-1'-yl-2-oxo-1-phenylethyl)-3-(4-chlorophenyl)urea,
(R)-1-(4-chlorophenyl)-3-{1-(4-hydroxyphenyl)-2-[4-(4-methylpiperazin-1-yl)-piperidin-1-yl]-2-oxoethyl}urea,
(R)-1-(4-chlorophenyl)-3-{2-[4-(4-methylpiperazin-1-yl)piperidin-1-yl]-2-oxo-1-phenylethyl}urea,
(R)-1-(4-chlorophenyl)-3-[2-(4-morpholin-4-ylpiperidin-1-yl)-2-oxo-1-thiophen-2-ylethyl]urea,
(R)-1-(2-[1,4']bipiperidinyl-1'-yl-2-oxo-1-thiophen-2-ylethyl)-3-(4-chlorophenyl)urea,
(R)-1-(4-chlorophenyl)-3-{2-[4-(4-methylpiperazin-1-yl)piperidin-1-yl]-2-oxo-1-thiophen-2-ylethyl}urea,
(R)-1-(4-chlorophenyl)-3-[2-(1'-methyl-4,4'-bipiperidinyl-1-yl)-2-oxo-1-(2-chlorophenyl)ethyl]urea,
(R)-1-(4-chlorophenyl)-3-[2-(4,4'-bipiperidinyl-1-yl)-2-oxo-1-(2-chlorophenyl)ethyl]-urea,
(R)-1-(4-chlorophenyl)-3-[1-(2-chlorophenyl)-2-(1'-methyl-2'-oxo-4,4'-bipiperidinyl-1-yl)-2-oxoethyl]urea,
(R)-1-(4-chlorophenyl)-3-[1-phenyl-2-(1'-methyl-2'-oxo-4,4'-bipiperidinyl-1-yl)-2-oxoethyl]urea,
2-(1'-methyl-4,4'-bipiperidinyl-1-yl)-2-oxo-1-phenylethyl(R)-4-chlorophenyl)-carbamate,
2-4,4'-bipiperidinyl-1-yl-1-(2-chlorophenyl)-2-oxoethyl(R)-(4-chlorophenyl)-carbamate,
2-4,4'-bipiperidinyl-1-yl-2-oxo-1-phenylethyl(R)-(4-chlorophenyl)carbamate,
1-(2-chlorophenyl)-2-(1'-methyl-4,4'-bipiperidinyl-1-yl)-2-oxoethyl(R)-(4-chlorophenyl)carbamate,
1-(2-chlorophenyl)-2-(4-morpholin-4-ylpiperidin-1-yl)-2-oxoethyl(R)-(4-chlorophenyl)carbamate,
2-[1,4]bipiperidinyl-1'-yl-1-(2-chlorophenyl)-2-oxoethyl(R)-(4-chlorophenyl)-carbamate,
2-(4-morpholin-4-ylpiperidin-1-yl)-2-oxo-1-phenylethyl(R)-(4-chlorophenyl)-carbamate,
2-[1,4']bipiperidinyl-1'-yl-2-oxo-1-phenylethyl(R)-(4-chlorophenyl)carbamate,
1-(2-chlorophenyl)-2-[4-(4-methylpiperazin-1-yl)piperidin-1-yl]-2-oxoethyl(R)-(4-chlorophenyl)carbamate,
2-[4-(4-methylpiperazin-1-yl)piperidin-1-yl]-2-oxo-1-phenylethyl(R)-(4-chlorophenyl)carbamate,
1-(2,3-difluorophenyl)-2-(1'-methyl-4,4'-bipiperidinyl-1-yl)-2-oxoethyl(R)-(4-chlorophenyl)carbamate,
1-(2-fluorophenyl)-2-(1'-methyl-4,4'-bipiperidinyl-1-yl)-2-oxoethyl(R)-(4-chlorophenyl)carbamate,
1-(2-methoxyphenyl)-2-(1'-methyl-4,4'-bipiperidinyl-1-yl)-2-oxoethyl(R)-(4-chlorophenyl)carbamate,
and pharmaceutically acceptable salts and stereoisomers thereof, including mixtures thereof in all ratios.

19. A process for the preparation of a compound according to claim 1, said process comprising
a) for the preparation of compounds
X denotes NH and
Y denotes O,
reacting a compound of formula II

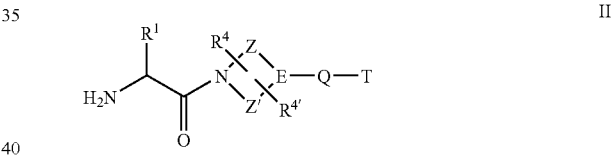

with a compound of formula III

D—N=C=O          III, or
b) for the preparation of compounds in which
X and Y denote O,
reacting a compound of formula IV

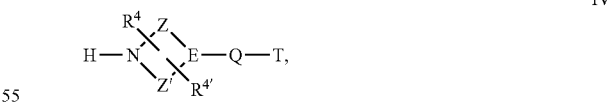

with a compound of formula V

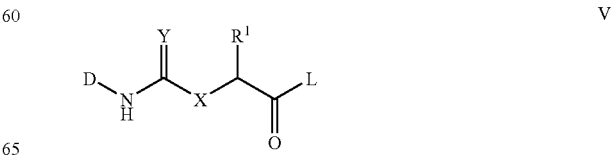

in which
X and Y denote O, and
L denotes Cl, Br, I or a free or reactively functionally modified OH group, and/or a base or acid of formula I is converted into one of its salts.

20. A pharmaceutical composition comprising a compound according to claim 1, and one or more excipients and/or adjuvants.

21. A pharmaceutical composition comprising a compound according to claim 1, and at least one further medicament active ingredient.

22. A kit comprising a first and second separate packs, said first pack containing an effective amount of a compound according to claim 1, and said second pack containing an effective amount of a further medicament active ingredient.

23. A compound according to claim 1, wherein Q is absent.

24. A compound according to claim 23, wherein X is $NR^3$ and Y is O.

25. A compound according to claim 23, wherein T is piperidin-1- or 4-yl, which is unsubstituted or monosubstituted by A and/or carbonyl oxygen (=O).

26. A compound according to claim 24, wherein T is piperidin-1- or 4-yl, which is unsubstituted or monosubstituted by A and/or carbonyl oxygen (=O).

27. A compound according to claim 23, wherein $R^1$ is phenyl which is unsubstituted or mono-, di- or trisubstituted by Hal, OH, or OA.

28. A compound according to claim 26, wherein $R^1$ is phenyl which is unsubstituted or mono-, di- or trisubstituted by Hal, OH, or OA.

29. A compound according to claim 23, wherein D is phenyl which is unsubstituted or mono- or disubstituted by Hal, A, hydroxyl, methoxy, ethoxy, hydroxycarbonyl, methoxycarbonyl or ethoxycarbonyl.

30. A compound according to claim 28, wherein D is phenyl which is unsubstituted or mono- or disubstituted by Hal, A, hydroxyl, methoxy, ethoxy, hydroxycarbonyl, methoxycarbonyl or ethoxycarbonyl.

31. A method of treating a patient suffering from thrombosis comprising administering to said patient an effective amount of a compound according to claim 1.

32. A compound according to claim 2, wherein T is piperidin-1- or 4-yl, which is unsubstituted or monosubstituted by A and/or carbonyl oxygen (=O).

33. A compound according to claim 32, wherein T is piperidinyl, 2-oxopiperidin-1-yl, or 2-oxopiperidin-4-yl, which in each case is optionally monosubstituted by A.

34. A compound according to claim 18, wherein said compound is selected from:

(R)-1-(4-chlorophenyl)-3-[2-(1'-methyl-4,4'-bipiperidinyl-1-yl)-2-oxo-1-phenylethyl]-urea,
(R)-1-(4-chlorophenyl)-3-[2-[4-(4-ethylpiperazin-1-yl)piperidin-1-yl]-2-oxo-1-phenylethyl]urea bistrifluoroacetate,
(R,R)-1-(4-chlorophenyl)-3-{2-methoxy-1-[1-(1'-methyl-4,4'-bipiperidinyl-1-yl)-methanoyl]propyl}urea trifluoroacetate,
(R,R)-1-(4-chlorophenyl)-3-(1-{1-[4-(4-ethylpiperazin-1-yl)piperidin-1-yl]-methanoyl}-2-methoxypropyl)urea bistrifluoroacetate,
(R)-1-(2-4,4'-bipiperidinyl-1-yl-2-oxo-1-phenylethyl)-3-(4-chlorophenyl)urea hydrochloride,
(R)-1-[2-4,4'-bipiperidinyl-1-yl-1-(4-hydroxyphenyl)-2-oxoethyl]-3-(4-chlorophenyl)-urea hydrochloride,
(R)-1-(2-4,4'-bipiperidinyl-1-yl-2-oxo-1-thiophen-2-ylethyl)-3-(4-chlorophenyl)urea hydrochloride,
(R)-1-(4-chlorophenyl)-3-[1-(4-hydroxyphenyl)-2-(1'-methyl-4,4'-bipiperidinyl-1-yl)-2-oxoethyl]urea trifluoroacetate,
(R)-1-(4-chlorophenyl)-3-[2-(1'-methyl-4,4'-bipiperidinyl-1-yl)-2-oxo-1-thiophen-2-ylethyl]urea trifluoroacetate,
(R)-1-(4-chlorophenyl)-3-[1-(4-hydroxyphenyl)-2-(4-morpholin-4-ylpiperidin-1-yl)-2-oxoethyl]urea trifluoroacetate,
1-[2-[1,4']bipiperidinyl-1'-yl-1-(4-hydroxyphenyl)-2-oxoethyl]-3-(4-chlorophenyl)-urea,
(R)-1-(4-chlorophenyl)-3-[2-(4-morpholin-4-ylpiperidin-1-yl)-2-oxo-1-phenylethyl]-urea trifluoroacetate,
(R)-1-(2-[1,4']bipiperidinyl-1'-yl-2-oxo-1-phenylethyl)-3-(4-chlorophenyl)urea trifluoroacetate,
(R)-1-(4-chlorophenyl)-3-1'-(4-hydroxyphenyl)-2-[4-(4-methylpiperazin-1'-yl)-piperidin-1-yl]-2-oxoethyl}urea bistrifluoroacetate,
(R)-1-(4-chlorophenyl)-3-{2-[4-(4-methylpiperazin-1-yl)piperidin-1-yl]-2-oxo-1-phenylethyl}urea bistrifluoroacetate,
(R)-1-(4-chlorophenyl)-3-[2-(4-morpholin-4-ylpiperidin-1-yl)-2-oxo-1-thiophen-2-ylethyl]urea trifluoroacetate,
(R)-1-(2-[1,4']bipiperidinyl-1'-yl-2-oxo-1-thiophen-2-ylethyl)-3-(4-chlorophenyl)urea trifluoroacetate,
(R)-1-(4-chlorophenyl)-3-{2-[4-(4-methylpiperazin-1-yl)piperidin-1-yl]-2-oxo-1-thiophen-2-ylethyl}urea bistrifluoroacetate,
(R)-1-(4-chlorophenyl)-3-[2-(1'-methyl-4,4'-bipiperidinyl-1-yl)-2-oxo-1-(2-chlorophenyl)ethyl]urea,
(R)-1-(4-chlorophenyl)-3-[2-(4,4'-bipiperidinyl-1-yl)-2-oxo-1-(2-chlorophenyl)ethyl]-urea,
(R)-1-(4-chlorophenyl)-3-[1-(2-chlorophenyl)-2-(1'-methyl-2'-oxo-4,4'-bipiperidinyl-1-yl)-2-oxoethyl]urea,
(R)-1-(4-chlorophenyl)-3-[1-phenyl-2-(1'-methyl-2'-oxo-4,4'-bipiperidinyl-1-yl)-2-oxoethyl]urea,
2-(1'-methyl-4,4'-bipiperidinyl-1-yl)-2-oxo-1-phenylethyl(R)-4-chlorophenyl)-carbamate,
2-4,4'-bipiperidinyl-1-yl-1-(2-chlorophenyl)-2-oxoethyl(R)-(4-chlorophenyl)-carbamate hydrochloride,
2-4,4'-bipiperidinyl-1-yl-2-oxo-1-phenylethyl(R)-(4-chlorophenyl)carbamate hydrochloride,
1-(2-chlorophenyl)-2-(1'-methyl-4,4'-bipiperidinyl-1-yl)-2-oxoethyl(R)-(4-chlorophenyl)carbamate trifluoroacetate,
1-(2-chlorophenyl)-2-(4-morpholin-4-ylpiperidin-1-yl)-2-oxoethyl(R)-(4-chlorophenyl)carbamate trifluoroacetate,
2-[1,4']bipiperidinyl-1'-yl-1-(2-chlorophenyl)-2-oxoethyl(R)-(4-chlorophenyl)-carbamate trifluoroacetate,
2-(4-morpholin-4-ylpiperidin-1-yl)-2-oxo-1-phenylethyl(R)-(4-chlorophenyl)-carbamate trifluoroacetate,
2-[1,4']bipiperidinyl-1'-yl-2-oxo-1-phenylethyl(R)-(4-chlorophenyl)carbamate trifluoroacetate,
1-(2-chlorophenyl)-2-[4-(4-methylpiperazin-1-yl)piperidin-1-yl]-2-oxoethyl(R)-(4-chlorophenyl)carbamate bistrifluoroacetate,
2-[4-(4-methylpiperazin-1-yl)piperidin-1-yl]-2-oxo-1-phenylethyl(R)-(4-chlorophenyl)carbamate bistrifluoroacetate,
1-(2,3-difluorophenyl)-2-(1'-methyl-4,4'-bipiperidinyl-1-yl)-2-oxoethyl(R)-(4-chlorophenyl)carbamate,
1-(2-fluorophenyl)-2-(1'-methyl-4,4'-bipiperidinyl-1-yl)-2-oxoethyl(R)-(4-chlorophenyl)carbamate, and
1-(2-methoxyphenyl)-2-(1'-methyl-4,4'-bipiperidinyl-1-yl)-2-oxoethyl(R)-(4-chlorophenyl)carbamate.

35. A compound according to claim 1, wherein T is cyclohexyl which is optionally mono-, di- or trisubstituted by =O, =S, =NH, =NR$^3$, =NOR$^3$, =NCOR$^3$, =NCOOR$^3$, =NOCOR$^3$, R$^3$, Hal, A, —[C(R$^3$)$_2$]$_n$—Ar, —[C(R$^3$)$_2$]$_n$-Het, —[C(R$^3$)$_2$]$_n$-cycloalkyl, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^2$ and/or S(O)$_n$A.

36. A compound according to claim 35, wherein T is unsubstituted cyclohexyl.

37. A compound according to claim 1, wherein T is piperidinyl, which is optionally mono-, di- or trisubstituted by =O, =S, =NH, =NR$^3$, =NOR$^3$, =NCOR$^3$, =NCOOR$^3$, =NOCOR$^3$, R$^3$, Hal, A, —[C(R$^3$)$_2$]$_n$—Ar, —[C(R$^3$)$_2$]$_n$-Het, —[C(R$^3$)$_2$]$_n$-cycloalkyl, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^2$ and/or S(O)$_n$A.

38. A compound according to claim 1, wherein T is piperazinyl which is optionally mono-, di- or trisubstituted by =O, =S, =NH, =NR$^3$, =NOR$^3$, =NCOR$^3$, =NCOOR$^3$, =NOCOR$^3$, R$^3$, Hal, A, —[C(R$^3$)$_2$]$_n$—Ar, —[C(R$^3$)$_2$]$_n$-Het, —[C(R$^3$)$_2$]$_n$-cycloalkyl, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^2$ and/or S(O)$_n$A.

39. A compound according to claim 1, wherein T is morpholinyl which is optionally mono-, di- or trisubstituted by =O, =S, =NH, =NR$^3$, =NOR$^3$, =NCOR$^3$, =NCOOR$^3$, =NOCOR$^3$, R$^3$, Hal, A, —[C(R$^3$)$_2$]$_n$—Ar, —[C(R$^3$)$_2$]$_n$-Het, —[C(R$^3$)$_2$]$_n$-cycloalkyl, OR$^3$, N(R$^3$)$_2$, NO$_2$, CN, COOR$^3$, CON(R$^3$)$_2$, NR$^3$COA, NR$^3$CON(R$^3$)$_2$, NR$^3$SO$_2$A, COR$^3$, SO$_2$NR$^2$ and/or S(O)$_n$A.

* * * * *

UNITED STATES PATENT AND TRADEMARK OFFICE
CERTIFICATE OF CORRECTION

| | |
|---|---|
| PATENT NO. | : 7,951,804 B2 |
| APPLICATION NO. | : 10/582850 |
| DATED | : May 31, 2011 |
| INVENTOR(S) | : Cezanne et al. |

It is certified that error appears in the above-identified patent and that said Letters Patent is hereby corrected as shown below:

Column 32, line 17 reads "(R)-1-(4-chlorophenyl)-3-1'-(4-hydroxyphenyl)-2-[4-(4-" should read -- (R)-1-(4-chlorophenyl-3-{1-(4-hydroxyphenyl)-2-[4-(4- --

Signed and Sealed this
Ninth Day of August, 2011

David J. Kappos
*Director of the United States Patent and Trademark Office*